United States Patent [19]

Emil et al.

[11] 4,003,370
[45] Jan. 18, 1977

[54] BLOOD PRESSURE MONITOR SYSTEM AND METHOD

[75] Inventors: Tuncay Emil, Fountain Valley; Kenneth Elmer Stack, Laguna Hills, both of Calif.

[73] Assignee: American Hospital Supply Corporation, Evanston, Ill.

[22] Filed: Oct. 14, 1975

[21] Appl. No.: 622,209

[52] U.S. Cl. .................. 128/2.05 D; 73/398 AR
[51] Int. Cl.² ........................................ A61B 5/02
[58] Field of Search ............... 128/2.05 D, 2.05 E; 73/398 AR, 402

[56] References Cited

UNITED STATES PATENTS

| | | | |
|---|---|---|---|
| 2,149,690 | 3/1939 | Snyder | 128/2.05 M |
| 3,088,323 | 5/1963 | Welkowitz et al. | 128/2.05 D |
| 3,495,585 | 2/1970 | Halligan et al. | 128/2.05 D |
| 3,545,431 | 12/1970 | Frank | 128/2.05 Q |
| 3,590,809 | 7/1971 | London | 128/2.05 D |
| 3,812,844 | 5/1974 | Sokol | 128/2.05 G |
| 3,817,106 | 6/1974 | Hobel | 128/2.05 D |
| 3,874,369 | 4/1975 | Pannier, Jr. et al. | 128/2.05 D |

*Primary Examiner*—William E. Kamm
*Attorney, Agent, or Firm*—Tilton, Fallon, Lungmus, Chestnut & Hill

[57] ABSTRACT

A compact, portable, self-contained unit includes a resistive strain gauge transducer for sensing blood pressure from an indwelling catheter to generate a signal representative of instantaneous pressure. This pressure signal is coupled to the signal inputs of a bank of comparator circuits having their outputs connected to associated ones of a string of light-emitting diodes (LEDs) connected in series across a source. The other inputs of the comparators are connected to associated nodes of a progressive reference voltage divider network. At any given time, all comparators having their signal inputs at a higher potential than their associated reference voltages will have their outputs "LOW," and those comparators having their signal inputs at a lower potential than their associated reference voltages will have their outputs "HIGH." Hence, a single LED is energized at any given time, and it represents the instantaneous pressure value. The value is easily read from a scale alongside the LEDs which are arranged in a line. Circuitry is also provided for measuring mean pressure which may be actuated by a push-button switch. Battery check circuitry and optical isolation are also provided.

15 Claims, 8 Drawing Figures

BLOOD PRESSURE MONITOR SYSTEM AND METHOD

BACKGROUND AND SUMMARY

The present invention relates to blood pressure measuring systems; and more particularly it relates to a system for measuring blood pressure and for generating a visual display representative of instantaneous blood pressure.

A number of ways have been suggested for measuring blood pressure, but there are two systems which currently have particularly widespread commercial use. One such system is the conventional pressure cuff which is used by general physicians and other technical personnel for obtaining a rough measure of systolic and diastolic pressures. In general, the systolic pressure is the maximum pressure occurring during ventricle contraction, and the diastolic pressure is a minimum pressure which occurs when the ventricle dilates. Because of the limitations on the instrument and the fact that the cuff is placed over an arm and a reading taken by ear, the resulting measurements are only estimates of the pressures being measured. Further, an actual pressure wave for a heartbeat is much more complex, containing a great deal of information above that contained in simple systolic and diastolic measurements. It is only known that the pressure wave varies depending upon the location of the pressure transducer, in the case of an indwelling transducer-for example, a transducer that is located in a blood vessel will yield a different pressure wave than one located in the heart, and there are differences even within the heart.

Thus, some cardiologists use a much more complex and costly system than the simple pressure cuff, and it includes a pressure transducer attached to a catheter located in a blood vessel or the heart for generating an electrical signal representative of instantaneous pressure. This signal is coupled through the catheter and displayed on an oscilloscope or equivalent device where it may be studied directly or recorded, as by photographing. In this manner, the complex signal representative of the heartbeat can be studied or recorded in various locations throughout the circulatory system.

In many cases, a physician might want to have more information regarding blood pressure than it is possible to obtain by means of a simple pressure cuff, but, for his purposes, he may not need all of the complex information contained in an oscillographic trace or photograph. It may also be that he does not have available to him the expensive equipment necessary to make an oscillographic recording, or the skilled technicians needed to operate it. The present invention is thus designed to fulfill this need. That is, it provides the accuracy of invasive techniques and permits measurement in different parts of the circulatory system, but it is neither as complicated to operate nor as costly as an oscilloscope system.

The present invention has still another use, which will be described below, after the invention has been described in detail, and this relates to the use of the invention as a monitor for the insertion of a temperature transducer in the pulmonary artery. Such a transducer, located in the pulmonary artery, may be used to measure blood flow, as described in the co-owned application of Tuncay Emil, Ser. No. 594,210, filed July 9, 1975, for "SYSTEM FOR COMPUTING CARDIAC FLOW RATES FROM THERMODILUTION MEASUREMENTS."

Briefly, the present invention is a compact, portable self-contained unit which includes a resistive strain gauge transducer for sensing blood pressure from an indwelling catheter to generate a signal representative of instantaneous pressure. This pressure signal is coupled to the signal (i.e., negative) inputs of a bank of comparator circuits. The output terminals of the comparators are connected to associated ones of a string of light-emitting diodes (LEDs). The LEDs are connected in series across a voltage source comprising conventional 1.5 volt battery.

The other (positive) inputs of the comparator circuits are connected to associated nodes of a progressive reference voltage divider network. Thus, each comparator compares the instantaneous pressure signal with a reference voltage so that at any given time, all comparators having their signal (i.e., negative) inputs at a higher potential than the reference voltages on their positive inputs will have their outputs "LOW," and those comparators having their signal inputs at a lower potential than their associated reference voltages will have their outputs "HIGH." Thus, a single "LED" is energized at any given time, and it represents the instantaneous pressure value being measured.

The LEDs are mounted to the fact of a cabinet housing the circuitry in a vertical line, and a scale is provided alongside the LEDs for making the measurement. Preferably, the hash marks of the scale are in register with the LEDs to facilitate reading of the scale.

In a preferred embodiment, more than one scale is provided; for example, two scales may be provided—one on either side of the string of LEDs. A slide has a central opening with a width just sufficient to permit viewing of the scale and one reading range in a first position; and when the slide is adjusted laterally to a second reading position, the scale and a second range of readings may be viewed. The circuitry includes a switch responsive to the position of the slide so that when the range is increased, the gain of the system may be correspondingly decreased.

Circuitry is also provided for measuring the mean or average pressure; and this circuitry is activated by a push button switch, thereby permitting the operator to obtain updated mean pressure information.

A pair of cursors are carried by a vertical rod mounted to the slide showing the scale, and the cursors are slidable along the rod for marking reference pressures, if desired. This is particularly useful when the system is used during catheter insertion or while the catheter is in situ to indicate change in a previously measured value.

An optically isolated output is also provided for recording instrumentation, if desired.

The cabinet which houses the electronic circuitry and on which the scale is formed is provided with a base or stand permitting it to be supported on a horizontal surface, such as a cabinet or table top. At the same time, the base is provided with an I.V. pole clamp to permit continuous monitoring of a patient during transport.

In using the present system, one sees a moving dot or point of light, and although the dot moves in discrete increments, there is nevertheless some continuity because of the rate at which it is traveling. On the other hand, because the dots are associated side-by-side with the hash marks of a scale, it is easy to observe specific maximum and minimum values by fixing one's eye on the scale. In the low range scale, one can read to within 1 mmHg, and in the high range, pressures are measured in increments of 2 mmHg.

Other features and advantages of the present invention will be apparent to persons skilled in the art from the following detailed description of a preferred embodiment accompanied by the attached drawing wherein identical reference numerals will refer to like parts in the various views.

THE DRAWING

DETAILED DESCRIPTION

Figure 1:
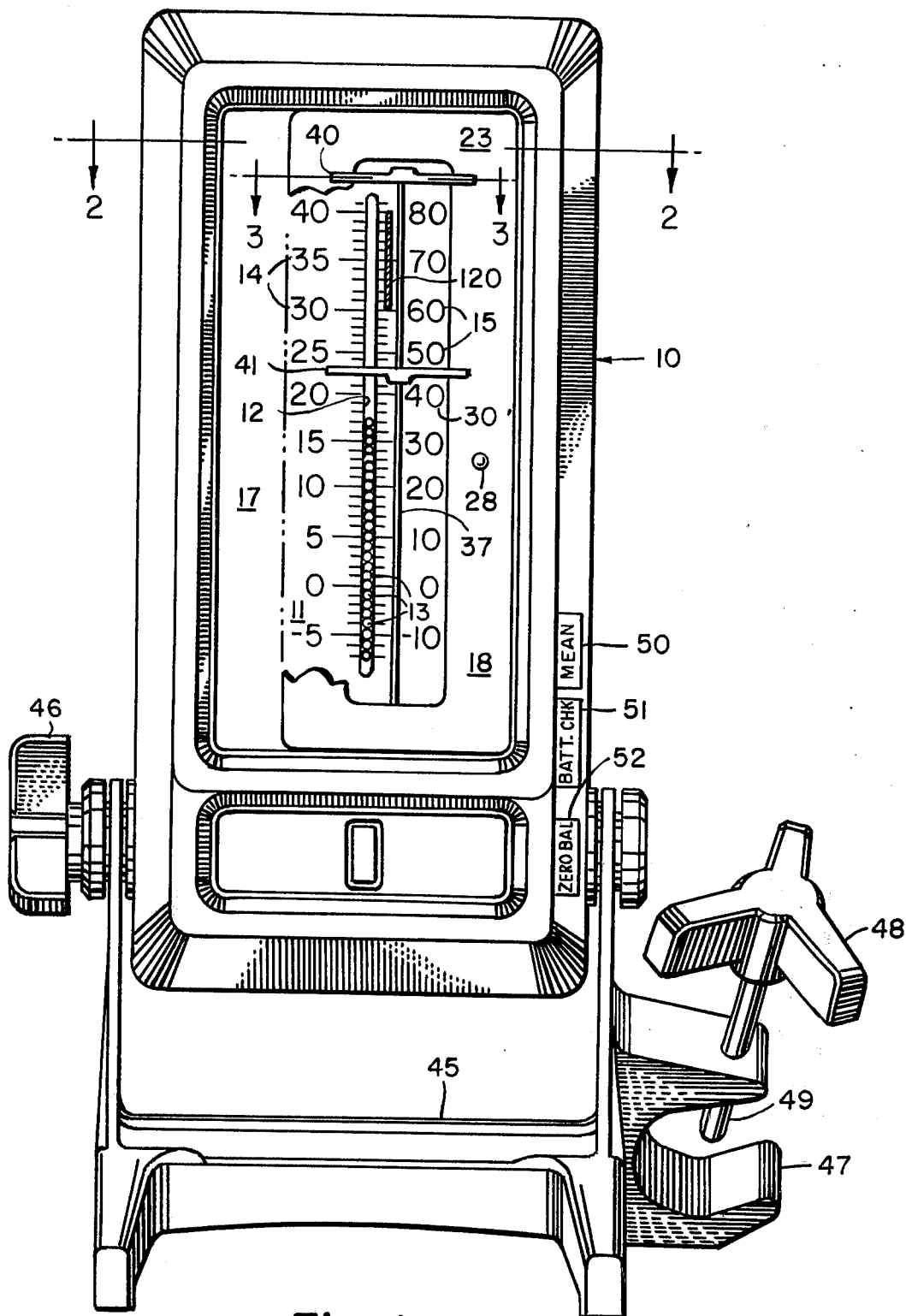
FIG. 1 is a front elevational view of an instrument incorporating the present invention, with portions broken away.

Referring first to FIG. 1, reference numeral 10 generally designates a cabinet which includes a display panel 11 marked with a scale. At the center of the scale there is a vertically elongated slot 12 behind which are mounted light-emitting diodes (LEDs) 13. The scale includes a low range including the numerals designated 14 to the left of the slot 12, and a high range, including the numerals designated 15 which are placed to the right of the slot 12.

Each of the scales 14, 15 are graduated in millimeters of mercury (mmHg). It will be observed that the low range has an elongated hash mark for each 5-millimeter increment and a smaller hash mark for each 1-millimeter measurement increment. The high range 15 is graduated in increments of 2 mmHg of pressure.

Figure 2:
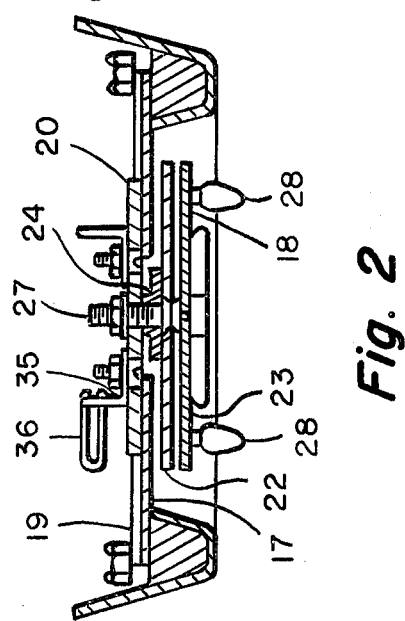
FIG. 2 is a fragmentary horizontal cross sectional view taken through the sight line 2—2 of FIG. 1 showing only the front portion of the cabinet.

The display panel 11 provides a faceplate to the cabinet 10. The rear surface of the display panel 11 has horizontal upper and lower grooves for mounting a slide assembly generally designated 18. The upper groove is shown at 19 in FIG. 2. In the groove 19 there is slidably received a guide member 20, located, it will be observed, behind the display panel 11. A slide subassembly comprising inner and outer rectangular slide members 22, 23 are located on the exterior of the display panel 11, spaced from the guide 20 by a spacer 24 and secured to it by means of a fastener 27, the head of which is embedded in the inner slide member 22. The outer slide member 23 is fixed to the inner slide member 22 by a pair of studs secured to the inner slide 22 and extending through the outer slide 23 and provided with caps 28 for moving the slide assembly left or right. The slot 19 is located, as noted, on the rear surface of the display panel 17, and above the top of the vertical slot 12. A similar arrangement for mounting the slide assembly is provided beneath the slot 12 to prevent parallelogramming during lateral movement. Both the inner slide 22 and the outer slide 23 have large central openings or windows which are the same size and register, the window for the outer slide 23 being shown and designated 30 in FIG. 1. The length of these windows is sufficient to display an entire scale range, but the width of the window is sufficient to display the slot 12, the graduation marks on either side of the slot 12, and only one of the scale ranges 14, 15. Thus, as seen in the position of FIG. 1, only the high-range scale 15 can be seen, although the left side of the slides is partially broken away for clarity. If the slide assembly is moved to the left, only the low range scale 14 can be seen.

To the rear of the guide 20 there is mounted a bracket 35, and an arm 36 is fixed to the bracket 35 for actuating a switch in the circuitry to be described to adjust the gain of the measuring circuitry depending upon the position of the slide assembly 18. In other words, when the slide is moved from the position shown to the left to permit the low-range scale to be used, the arm 36 actuates the switch to increase the gain of the measuring circuitry, as will be further described below. Other arrangements may be made wherein there are a number of scales and a slide mechanism which both adjusts the gain of the measuring circuitry and marks all but the proper scale for that gain.

Figure 3:
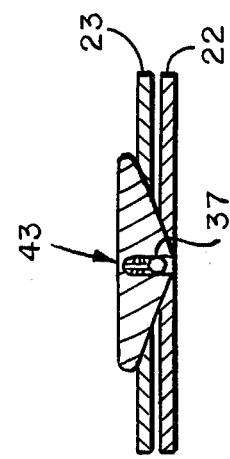
FIG. 3 is a horizontal cross sectional view, as seen from the bottom, of the slider assembly of the instrument.

Referring now to FIGS. 1 and 3, a rod 37 is embedded at its top and bottom in the upper and lower transverse portions of the outer slide 23. Upper and lower cursors 40, 41 are slidably mounted on the rod 37, using a spring and button assembly, generally designated by reference numeral 43 in FIG. 3 to provide a frictional engagement with the rod 37. Thus, the cursors 40, 41 may easily be moved along the rod 37, but they are held in place through friction with the rod after adjustment. These cursors may be used for temporarily recording the upper and lower limits of a range, if desired, or one cursor may be used for temporarily recording a mean pressure.

Referring again to FIG. 1, the lower portion of the cabinet 10 is pivotally mounted to a stand generally designated by reference numeral 45 which permits the unit to be mounted on a horizontal surface, such as a table or counter top. The cabinet 10 may be positioned about its horizontal mounting axis and held in place by means of a handwheel 46 which provides a friction clamp once the unit is adjusted. Further, the stand 45 is provided with means for mounting it to an I.V. pole, shown at 47 and including a handle 48 and a threaded stud 49 for engaging and frictionally clamping to the pole.

Also accessible from the front of the instrument are a push switch 50 which actuates circuitry for computing a mean pressure value, as distinguished from an instantaneous pressure value, a push switch 51 for checking the operability of the battery, and a thumbwheel 52 for balancing the zero level of an electrical bridge circuit, to be discussed.

Figure 4:
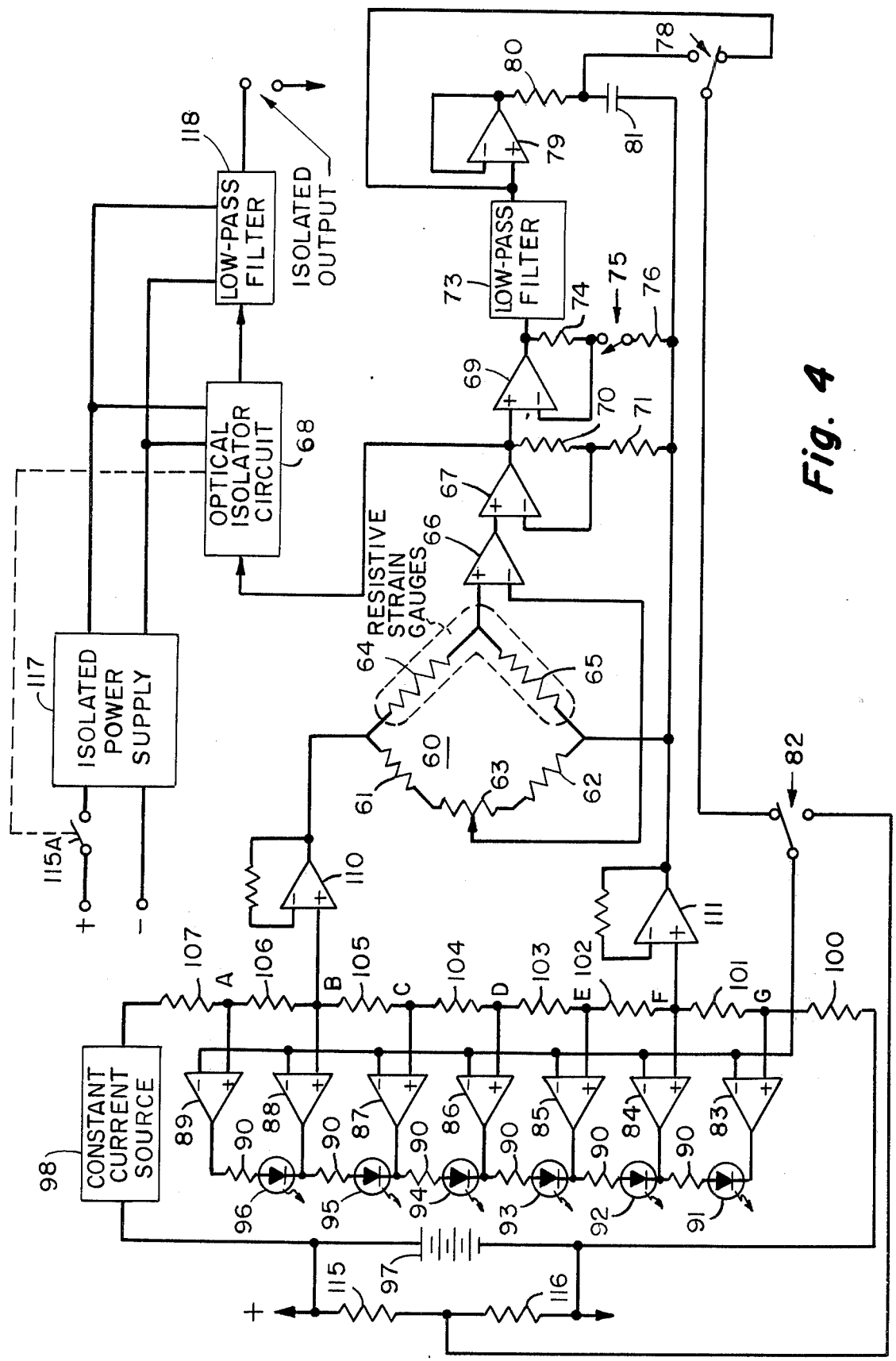
FIG. 4 is a circuit schematic diagram, partly in functional block form, of a measuring system for the instrument of FIG. 1.

Referring now to FIG. 4, reference numeral 60 generally designates a bridge circuit including a first fixed resistor 61, a second fixed resistor 62, a potentiometer 63 connected in series with the resistor 61, 62, and a pair of resistive strain gauges, designated respectively 64 and 65. The resistive strain gauge elements 64, 65 form the input transducer means which are responsive to the hemodynamic pressure of the patient and transform that pressure into an electrical signal representative of the blood pressure. A preferred transducer is disclosed in the co-owned application of Blake, et al. entitled "External Blood Pressure Transducer," Ser. No. 589,714, filed June 23, 1975. The transducer is coupled to the patient's blood by means of a pressure tube and a catheter which is inserted in the patient's pulmonary system. Briefly, the resistive strain gauge elements 64, 65 are mounted on a diaphragm in orthogonal relationship so that one senses compressive forces on the diaphragm and other senses tension forces, and the resultant signal is additive and representative of the sensed pressure.

The potentiometer 63 serves as a zero balance control which is actuated by the operator's movement of the zero balance thumbwheel 52, described above.

The output of the bridge 60, taken between the junction of the transducer elements 64, 65 and the movable arm of the potentiometer 63 is coupled to the inputs of a differential amplifier 66, which may be a conventional linear amplifier known as an instrumentation amplifier, as that term is used in the art.

The output of the amplifier 66 is connected to the positive input terminal of a differential amplifier 67. The output of the amplifier 67 is connected to an optical isolator circuit 68, to the positive input of a differential amplifier 69, and to a normalizing resistor 70. The other terminal of the normalizing resistor 70 is connected by means of a fixed resistor 71 to common, and to the negative input of the amplifier 67. The network including the normalizing resistor 70, the fixed resistor 71 and the connection to the negative input terminal of amplifier 67 permits the amplification section of the measuring system to be matched to the particular characteristics of the resistive strain gauges 64, 65. That is, the normalization resistor 70 is usually provided by the manufacturer of the transducer elements and matched to them to compensate for the particular sensitivity of a given set of transducers so that the resulting gain or sensitivity of the combination is a known value. As the value of the normalizing resistor 70 increases, the gain of amplifier 67 also increases, and the value of the resistor 70 would be selected relatively high in the case of less sensitive transducer elements.

The output of the amplifier 69 is coupled to a low-pass filter 73 and to a fixed resistor 74. The other terminal of the fixed resistor 74 is connected to the negative input of the amplifier 69 and to one terminal of a range switch 75, the other terminal of which is connected through a fixed resistor 76 to common. The range switch 75 is actuated by the arm 36 of FIG. 2 in such a manner that the switch 75 is closed when the slide 18 is in the left position in FIG. 1— i.e., when the low range scale is being used. In this position, the gain of the amplifier 69 and associated circuitry is 2. When the switch 75 is open (i.e., when the high range scale is being used) the gain of the amplifier is unity.

The low-pass filter 73 has a cutoff frequency of approximately 10 cycles per second, and its function is, of course, to block the passage of higher frequency signals.

The output of the low-pass filter 73 is connected to one terminal of a two-position switch 78 and to the positive input of a differential amplifier 79, arranged so that its gain is unity. The output of the amplifier 79 is connected to a resistor 80 which is connected in series with a capacitor 81, and the junction between these two is connected to a second terminal of the switch 78. The movable contact of the switch 78 is connected to a terminal of a second two-position switch 82.

In the position shown in the drawing, the switch 78 couples the output of the low-pass filter 73 directly to the readout circuitry, and this position is used for the measurement of instantaneous pressure. In the other position, the switch 78 couples a signal representative of the mean pressure to the readout circuitry. Hence, resistor 80 and capacitor 81 form an RC filter having a time constant of approximately 2.2 seconds—long enough so that the signal representative of instantaneous pressure will be averaged.

The function of switch 82 will be described below, but in the position shown, as mentioned, it couples the output of the amplification section to the readout circuitry.

Turning now to the left-hand portion of FIG. 4, the measurement signal is connected directly to the negative input terminals of a series of comparator circuits. In the illustrated embodiment there are seven comparator circuits, and these are designated respectively 83–89. There are only seven such circuits shown for simplicity, but it will be appreciated that there are as many comparator circuits as there are LEDs. In one commercial embodiment, there are 50 LEDs. The comparator circuits 83–89 also may be of conventional design, and they operate such that each circuit generates a "HIGH" output when the potential on its positive input is higher than that on its negative input. Conversely, the output is "LOW" when the potential on its positive input is lower than the potential on its negative input.

Between the outputs of each adjacent pair of comparator circuits, there is a series circuit comprising a resistor and an LED. The resistors are all designated 90, and the LEDs are designated respectively 91–96. Thus, each LED is associated with a pair of the comparators 83–89, and an individual LED is energized only when the outputs of its associated pair of amplifiers are respectively LOW and HIGH. For example, the LED 94 is energized or lit only when the output of amplifier 86 is LOW and the output of amplifier 87 is HIGH. Only one LED can be energized at any given time, as will be explained more fully presently.

A battery 97, which may comprise four individual cells, has one terminal connected to a constant current source 98. The constant current source 98 feeds a resistive divider network comprising eight resistors, designated respectively 100–107. All of the resistors 100–107 may be of equal value. The combination of the constant current source and resistive divider network thus forms a series of progressively increased reference voltages, the highest voltage being present at the node A, the next highest at the node B, and so on. The nodes A-G are connected respectively to the positive input terminals of the comparators, as illustrated.

Node B is also connected to the positive input of a unity gain amplifier 110, the output of which provides the reference voltage for bridge 60; and similarly, node F is also connected to the positive input of the unity gain amplifier 111, the output of which provides system common.

The circuitry described thus far operates as follows: the strain gauge elements 64, 65 are responsive to instantaneous blood pressure and generate a corresponding electrical signal, in the bridge circuits 60, which represents blood pressure. This signal is amplified by the amplifier 66, and the signal is normalized by the amplifier 67 and its associated circuitry. The output of the amplifier 67 is then left at unity or amplified by a predetermined number, depending upon the position of the range switch 75.

The output of the amplifier 69 is passed through the low-pass filter 73, and assuming switches 78 and 82 are in the position illustrated, this signal is coupled to the negative input terminals of the comparator circuits 83–89. Assuming, for example, that the voltage on the negative inputs is higher than the voltage at the node D of the reference voltage network, but lower than the voltage at node C, the output of comparator 82 will be LOW (because its positive input is at a potential lower than its negative input), and the output of comparator 87 will be HIGH (because its positive input is at a potential higher than its negative input). Thus, the LED 94 is energized. The LEDs 91–93 are not energized because the outputs of all comparators 83–86 are LOW; and similarly, the LEDs 96, 96 are not energized because the outputs of comparators 87–89 are all HIGH. As the measured voltage varies, so will its relationship to the voltages at the reference nodes A–G, thereby energizing different individual ones of the LEDs 91–96. In all cases, only one LED will be energized, and that energized LED will be representative of the instantaneous input voltage. This, in combination with the measuring scales already described enables accurate, simple and fast interpretation of the results.

Referring now to the extreme left-hand portion of FIG. 4, two fixed resistors 115 and 116 are connected in series across the battery 97, and the junction between them is connected to the second fixed terminal of switch 82. The resistors 115, 116 are of relatively high value so as to avoid draining the battery 97, and the resistor 116 is larger in value. As long as the battery 97 has a terminal voltage in the useful range (that is, higher than a predetermined value) its actual terminal voltage will not affect the reference voltages generated at the nodes A–G. When the switch 82 (which may be a momentary contact switch) is actuated, the voltage across resistor 116 is coupled to the negative input terminals of the comparators, and it will thus be compared with the reference voltages at the higher nodes. The reference voltages do not change even though the battery voltage may deteriorate because of the constant current source. The system is designed so that if the terminal voltage of battery 97 is acceptable, then an LED within the range defined by the solid marker 120 in FIG. 1 on the display scale, will be energized, thereby signifying that the battery need not be replaced. The switch 82 is actuated by the push tab 51 on the front of the instrument panel. Similarly, the push tab 50 actuates the averaging switch 78 to couple the output of the averaging network (resistor 80 and capacitor 81) to the negative input terminals (sometimes called the "signal" inputs) of the comparators. This energizes a single LED representative of the mean value of blood pressure.

As previously mentioned, the output signal of the amplifier 67 is coupled to an optical isolator circuit 68. The optical isolator circuit 68 may be of conventional design including an input stage and a matching output stage. The two stages are separated by a manually actuated switch which is coupled mechanically to a switch designated 115A. When the switch 115A is closed, it couples the battery to the isolated power supply 117, and the output power of the supply 117 is coupled to the output stage of the optical isolator circuit 68 and to a low-pass filter circuit 118 which may include active circuits. Thus, the output of the low-pass filter circuit 118 provides an isolated output for recording instrumentation, if desired. When the switch 115A is opened, the power supply 117 is de-energized, and the optical isolator circuit 68 is interrupted.

SYSTEM USE DURING CATHETER PLACEMENT

As indicated above, in measuring cardiac output flow using a thermodilution procedure, it is necessary to place a thermistor in the pulmonary artery. Such a thermistor may be located near the tip of a catheter, such as the Swan-Ganz catheter Model 93A-118-7F, manufactured by Edwards Laboratories of Santa Ana, Calif.

The catheter is inserted in an artery in the arm, and the catheter tip then proceeds to the heart area, passing first into the right atrium, then the right ventricle, and thence into the pulmonary artery. As the catheter tip continues, it will assume the pulmonary capillary wedge position, and from this position, it is backed off slightly, at which location the thermistor is properly in place for measuring cardiac flow.

Figure 5:
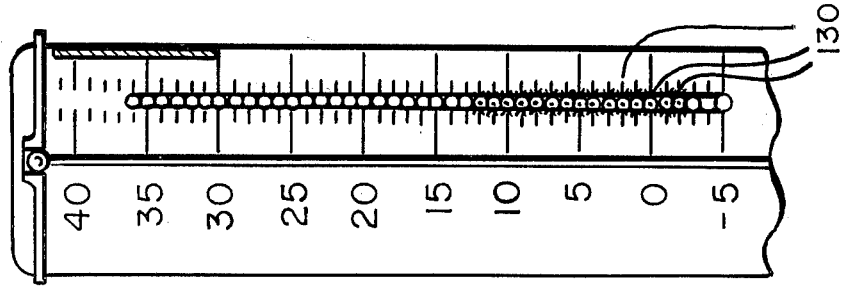

It is known that the range of pressure levels in the four locations mentioned above are different, and the present invention may be used to monitor the location of the tip of the catheter during these various stages. For example, referring to FIG. 5, it is known that when the tip of the catheter is in the right atrium, the sensed pressure will be in the range of approximately 0–12 mmHg. In FIG. 5, the lighted dots 130 are not all lit at the same time, of course, but this illustration is taken over a time lapse so as to indicate the range of pressures encountered which are indicative of the location of the tip of the catheter.

Figure 6:
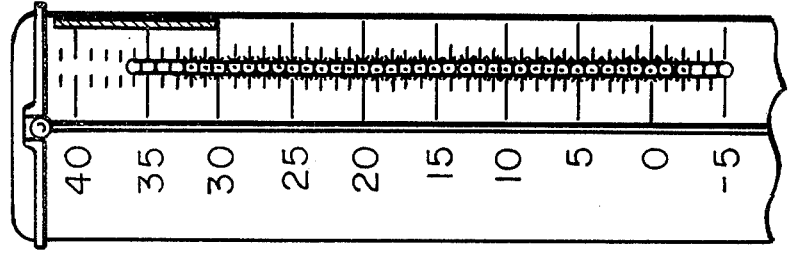

When the tip of the catheter enters the right ventricle, the pressure range increases to 0–32 mmHg, as indicated in FIG. 6. These pressure ranges are only representative, and they will, of course, change somewhat from case to case.

Figure 8:
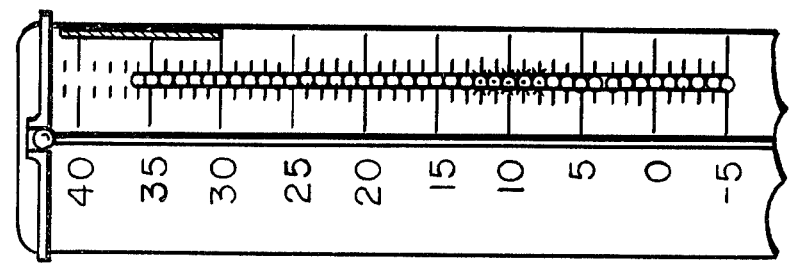
FIGS. 5–8 are fragmentary views of the scale of the instrument of FIG. 1 which illustrate use of the inventive system during catheter insertion.
Figure 7:
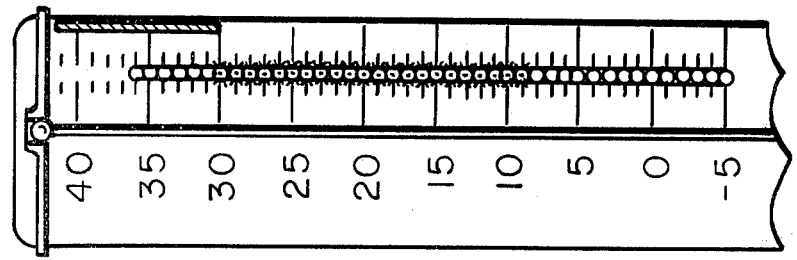

Turning now to FIG. 7, the light dots indicated as being illuminated represent the pressure range that will be sensed when the tip of the catheter is in the pulmonary artery. In this example, the range is 9–30 mmHg. Finally, in FIG. 8, when the catheter tip is in the pulmonary capillary wedge position, the pressure range reduces to approximately 8–12 mmHg, as illustrated by the illuminated light dots in FIG. 8. It is also known that the mean or average pressure in the capillary wedge position is equal to the low pressure for the range of FIG. 7 when the catheter tip is in the pulmonary artery; hence, a person may use the lower cursor 41 to mark the lower limit of the range of FIG. 7, and then either use that cursor to determine when a catheter tip is in the pulmonary wedge position when it falls in the midrange of the pressures being measured, or when he thinks the catheter tip is in the pulmonary wedge position, he may actuate the mean switch 78 which will illuminate a single light dot which will be in approximately the same position as the cursor. For proper placement, of course, the catheter tip is then withdrawn from the pulmonary capillary wedge position to insure location in the pulmonary artery.

It can thus be seen that the present invention provides a simple and economical means for monitoring the location of the catheter during insertion, as contrasted to the more conventional method of using an oscilloscope to continuously display the pressure waveform present at the catheter tip. This latter method is not only more cumbersome and difficult to interpret, but is extremely costly in terms of the equipment that is required.

Having thus described in detail a preferred embodiment of the present invention, persons skilled in the art will be able to modify certain of the structure which has been illustrated and to substitute equivalent elements for those disclosed, while continuing to practice the principle of the invention; and it is, therefore, intended that all such modifications and substitutions be covered as they are embraced within the spirit and scope of the appended claims.

We claim:

1. Apparatus for measuring blood pressure comprising: transducer means sensing blood pressure for generating a signal representative of instantaneous pressure; reference voltage source means for generating a plurality of reference signals of progressively increasing magnitude; a plurality of light-emitting circuit means connected in series; and a plurality of comparator circuit means, each having an output connected to a junction between adjacent ones of said light-emitting circuit means, each comparator circuit means further having a first input connected to an associated reference signal of said reference voltage source means, and a second input receiving said signal representative of instantaneous pressure; whereby all comparator circuits having their first inputs at a higher potential than their associated reference voltages will have their outputs at a first level, and all comparator circuits having their signal inputs at a lower potential than their associated reference voltages will have their outputs at a second level, and one light-emitting circuit means will be energized and representative of the sensed pressure.

2. The apparatus of claim 1 wherein said reference voltage source means comprises a plurality of resistors connected in series, the nodes between adjacent resistors being connected to the respective first input terminals of said comparator circuit means; and constant current source means supplying constant current to said series-connected resistors.

3. The apparatus of claim 1 wherein said light-emitting circuit means are arranged in a line and in an order representative of the magnitude of pressure, said system further comprising means providing a scale adjacent said line of light-emitting circuit means to facilitate reading thereof.

4. The apparatus of claim 1 wherein said transducer means comprises resistive strain gauge means in communication with hemodynamic pressure transmitting means, said system further comprising bridge circuit means including said strain gauge means for generating said signal representative of pressure.

5. The apparatus of claim 1 further comprising switch means having at least a first and a second position, said switch coupling said pressure signal to said comparator circuit means in a first position, said system further comprising signal averaging circuit means receiving said signal representative of pressure for generating an output signal representative of the average pressure, said switch means connecting the output of said signal averaging circuit means to said comparator circuit means in said second position.

6. The apparatus of claim 1 further comprising battery means for supplying electrical energy to said reference voltage source means; a resistive divider network connected across the terminals of said battery; and selective switch means for selectively connecting said voltage divider circuit means across said battery to said second input terminals of said comparator circuit means, whereby one of said light-emitting circuit means will be energized in accordance with the terminal voltage of said battery means.

7. The apparatus of claim 1 wherein said light-emitting circuit means are arranged in a line and in an order corresponding to the order in which its associated comparator circuit responds to an analog input signal, said system further comprising means providing a scale adjacent said light-emitting circuit means, said scale including a first range and a second range, said apparatus further comprising a slide movable between a first position and a second position and defining a window for displaying said line of light-emitting circuit means and one of said scale ranges while shielding the other in each of said first and second positions.

8. The apparatus of claim 7 further comprising a cabinet for housing said reference voltage source means, said light-emitting circuit means, and said comparator circuit means, and including a display panel adjacent said slider means, said apparatus further comprising a stand rotatably mounted to said cabinet and adapted to support said cabinet on a horizontal surface.

9. The apparatus of claim 1 further comprising a cabinet for housing the circuitry and including a display panel adjacent said light-emitting circuit means arranged in a line, said display panel including scale means associated with the arrangement of said light-emitting circuit means.

10. The apparatus of claim 9 wherein said scale means includes first indicia representative of a high range and second indicia representative of a low range, said system further comprising a slide having a window dimensioned to display said diodes and only one of said scales, said system further including amplifier means receiving the output signal as a transducer means for amplifying the same; circuit means including a switch for adjusting the gain of said amplifier means; and means movable with said slide for actuating said gain-adjusting switch whereby as said slide is moved to display a low range, the amplification of said amplifier means is increased.

11. The apparatus of claim 10 further comprising averaging circuit means receiving the output signal of said amplification means; and average switch means for selectively connecting either said amplification means or said averaging circuit means to said second inputs of said comparator circuit means.

12. Apparatus for measuring blood pressure comprising: transducer means sensing blood pressure for generating a signal representative of instantaneous pressure, a cabinet with a display panel and including indicia on said panel providing a scale; a plurality of light-emitting circuit means connected in series and arranged in a line adjacent said scale; and circuit means receiving said pressure signal for energizing only one of said light-emitting circuit means at a time and in such a manner that the energized light-emitting circuit means displays a value in relation to said scale which is representative of blood pressure.

13. The apparatus of claim 12 wherein said display panel includes a plurality of sets of indicia, each representative of a different scale and aligned with said light-emitting circuit means and further comprising selection means for selecting one of said scales at a time for use with said light-emitting circuit means, said circuit means having a variable gain amplification circuit and said selection means being further operative to vary the gain of said amplification circuit in accordance with the scale selected for use.

14. A method of determining the location of the tip of a catheter during introduction of the catheter through the venous system into the pulmonary artery, the tip of said catheter being provided with a pressure transducer, comprising: sensing the instantaneous blood pressure at said catheter tip; converting the sensed pressure to an electrical analog signal representative of the sensed pressure; providing a series of light-emitting circuit means in a line wherein each light-emitting circuit means corresponds to a different pressure value; and energizing only one light-emitting circuit means at a time with said analog signal and in such manner that the energized light-emitting circuit means in positional relation to the non-energized light-emitting circuit means is representative of the magnitude of the sensed blood pressure, and the range of energized light-emitting circuit means is representative of the location of the tip of the catheter as it transgresses through the venous system into the pulmonary artery.

15. A method of invasively measuring blood pressure comprising: introducing a catheter into the circulatory system of a person; sensing the instantaneous blood pressure at the tip of the catheter; converting the sensed pressure to an electrical analog signal representative of the sensed pressure; providing a series of light-emitting circuit means in a line wherein each light-emitting circuit means corresponds to a different pressure value, and energizing only one light-emitting circuit means at a time with said analog signal and in such manner that the energized light-emitting circuit means in positional relation to the non-energized light-emitting circuit means is representative of the magnitude of the sensed blood pressure.

* * * * *